United States Patent [19]

Wolff

[11] 4,194,125
[45] Mar. 18, 1980

[54] SUNLAMP AND SOURCE OF ULTRAVIOLET RADIATION THEREFOR

[76] Inventor: Friedrich Wolff, Lindenring 17, D-6000 Frankfurt am Main 50, Fed. Rep. of Germany

[21] Appl. No.: 958,613

[22] Filed: Nov. 8, 1978

[30] Foreign Application Priority Data

Oct. 16, 1978 [DE] Fed. Rep. of Germany ....... 2844967

[51] Int. Cl.² .............................................. G01J 1/00
[52] U.S. Cl. .................................... 250/504; 313/112
[58] Field of Search ............... 250/493, 494, 503, 504; 313/112; 240/21, 52 R

[56] References Cited

U.S. PATENT DOCUMENTS

| | | | |
|---|---|---|---|
| 4,048,537 | 9/1977 | Blaisdell | 313/112 |
| 4,103,175 | 7/1978 | Levin | 250/504 |

*Primary Examiner*—Bruce C. Anderson
*Attorney, Agent, or Firm*—Peter K. Kontler

[57] ABSTRACT

A sunlamp with one or more pairs of aligned sockets for the prongs of plugs which are secured to the end portions of a tubular source of ultraviolet radiation in the UVA range and the neighboring portion of the UVB range. The combined length of the source and plugs is between 440 and 450 mm so that the source cannot be inserted into the sockets of a standard lamp using tubular sources of fluorescent light. The souce is connected in circuit with a timer which interrupts the emission of ultraviolet radiation after a preselected interval of tanning.

7 Claims, 3 Drawing Figures

SUNLAMP AND SOURCE OF ULTRAVIOLET RADIATION THEREFOR

BACKGROUND OF THE INVENTION

The present invention relates to improvements in sunlamps and to improvements in sources of ultraviolet radiation which can be used in sunlamps.

My U.S. Pat. No. 4,095,113 (the disclosure of this patent is incorporated herein by reference) describes a sunlamp which can employ a substantial number (e.g., between 5 and 20) discrete elongated sources of ultraviolet radiation. The sources are parallel to each other and their envelopes preferably constitute filters which intercept radiation except in the so-called UVA region and preferably also in the upper part of the so-called UVB region. The envelopes can be filled with mercury vapors and their internal surfaces may be coated with a layer or film of radiation producing material in a manner as disclosed in the aforesaid patent. The arrangement is such that the sources cooperate with reflector means (e.g., of the type disclosed in my U.S. Pat. No. 4,106,083 granted Aug. 8, 1978) to establish a high-density radiation field close to the exit opening or openings of the reflector means. A person desirous of rapidly acquiring a tan places his or her body or a selected portion of the body into close proximity of the opening or openings.

It is advisable to insure that radiation sources which are utilized in a sunlamp (e.g., a sunlamp of the type disclosed in the aforesaid patent) cannot be used in other types of lamps, for example, in lamps whose fixtures can accept standard sources of fluorescent light. This will be readily appreciated since excessive exposure of persons occupying the area which is illuminated by one or more sources of ultraviolet radiation could cause sunburn or other undesirable effects. It is equally desirable to insure that a sunlamp be designed in such a way that it cannot accept standard sources of fluorescent light, i.e., light sources (such as neon lamps) which are not designed to emit ultraviolet radiation. For example, a person desirous of acquiring a tan could be exposed to radiation issuing from tubular light sources of the type customarily employed in the field of photography; exposure to radiation issuing from such sources could be harmful to the person who expects to acquire a tan.

One of the solutions which appear to be close at hand is to equip the sunlamps with special sockets which are designed in such a way that they cannot accept the contacts and/or plugs of conventional radiation sources, i.e, of sources other than those which are specifically designed to emit radiation in the ultraviolet region. For example, it is possible to replace pairs of standard electric contacts at each end of an elongated tubular radiation source with a single oval projection having two terminals embedded therein and to equip the housing of the sunlamp with special sockets which can accept such oval projections. The just discussed light sources and sockets therefor are available on the market; however, they are used only in connection with light sources whose tubular envelopes have a diameter of approximately 40 mm.

Many tubular light sources whose light output is relatively low comprise envelopes with an outer diameter of approximately 25 mm. As a rule, the length of such tubular light sources is 437.4 mm (according to US Standard C 78.404-1964). The end portions of these light sources carry plugs with pairs of standard pin-shaped electric contacts which are removably insertable into complementary sockets. A light source which is designed to emit ultraviolet radiation in the UVA region (and perhaps in the upper part of the UVB region) and which has the just mentioned dimensions could be readily inserted into the sockets of standard light fixtures which is undesirable for the aforementioned reasons. A modification of the sockets and plugs (including the prongs) is not economical in view of the relatively small number of such sources of ultraviolet radiation (especially when compared with the number of radiation sources whose outer diameter is approximately 40 mm). Therefore, the provision of sources of ultraviolet light having an outer diameter of approximately 25 mm and a length of 437.4 mm with specially designed plugs, prongs or projections and sockets would contribute excessively to the initial cost of such commodities.

OBJECTS AND SUMMARY OF THE INVENTION

An object of the invention is to provide a novel and improved source of ultraviolet radiation whose cost is relatively low and which is constructed in such a way that it cannot be inserted into light fixtures other than sunlamps.

Another object of the invention is to provide a sunlamp which embodies one or more improved sources of ultraviolet radiation and which cannot accept standard tubular light sources.

A further object of the invention is to provide a tubular source of ultraviolet radiation which, though similar to conventional sources of fluorescent light, cannot be inserted into fixtures which are designed to accept standard sources of fluorescent light.

An additional object of the invention is to provide a source of ultraviolet light which can be manufactured at the cost of standard sources of fluorescent light.

One feature of the invention resides in the provision of a source of ultraviolet radiation, particularly in the UVA region and preferably also in the adjacent portion of the UVB region. The improved source comprises an elongated hollow tubular body having first and second end portions and an outer diameter of approximately 25 mm, a plug at each of the two end portions, and electric contacts extending from each of the plugs. The combined length of the tubular body and the two plugs is between 440 and 450 mm, preferably approximately 445 mm and most preferably between 444.5 and 445.5 mm. Such light source cannot be installed in lamps which are designed to receive standard sources of fluorescent light.

Another feature of the invention resides in the provision of a sunlamp which comprises a housing with spaced-apart aligned first and second sockets which can removably receive the contacts of the above outlined radiation source. The housing preferably comprises or contains a reflector which partially surrounds the properly inserted source and the sunlamp preferably further comprises a suitable timer which is in circuit with the contacts and is designed to automatically terminate the emission of radiation after a preselected interval of time to thus insure that a person desirous of acquiring a tan is not exposed to radiation for a period which is long enough to result in sunburn or other deleterious effects.

The novel features which are considered as characteristic of the invention are set forth in particular in the appended claims. The improved sunlamp itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
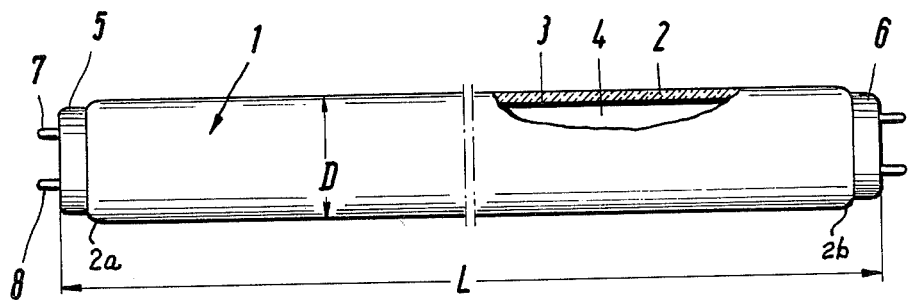
FIG. 1 is a fragmentary side elevational view of a source of ultraviolet radiation which embodies the invention, with a portion of the tubular body broken away.
Figure 3:
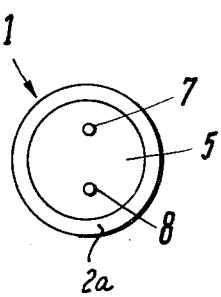
FIG. 3 is an end elevational view of the radiation source.

FIGS. 1 and 3 show a source 1 of ultraviolet radiation which comprises an elongated hollow tubular body 2 with an outer diameter D of approximately 25 mm. The internal surface of the body 2 is coated with a film or layer 3 of radiation emitting material, and the interior 4 of the body 2 contains a supply of mercury vapors with or without additives. The end portions 2a and 2b of the body 2 are sealed and are respectively connected with plugs 5 and 6 each of which carries two electric contacts or prongs 7 and 8 extending in parallelism with the axis of the body 2. The combined length L of the tubular body 2 and plugs 5, 6 is between 440 and 450 mm, preferably approximately 445 mm with a tolerance of ±0.5 mm (i.e., between 444.5 and 445.5 mm). The body 2 consists of glass. When the film 3 is energized on completion of the electric circuit via contacts 7 and 8, it emits substantial amounts of ultraviolet radiation, especially in the UVA region. The material of the tubular body 2 constitutes a filter which intercepts radiation in regions other than the UVA region. The nature of the filter is preferably such that it invariably intercepts ultraviolet radiation in the UVB region below 295 nanometers. Thus, the body 2 permits the emission of radiation in the UVA region and preferably also in the upper part of the UVB region (above 295 nm).

Figure 2:
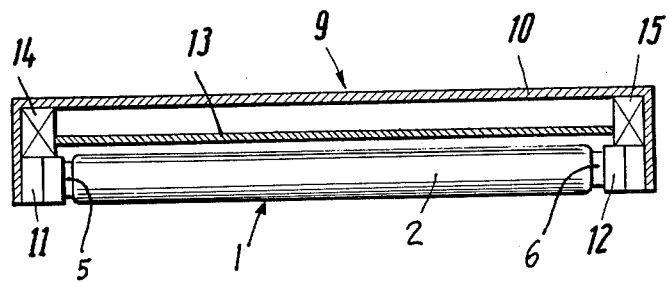
FIG. 2 is a longitudinal sectional view of the housing of a sunlamp which can utilize radiation sources of the type shown in FIG. 1.

FIG. 2 shows a sunlamp 9 which can utilize one or more sources 1. The sunlamp 9 comprises a housing 10 having two end portions which carry spaced-apart aligned sockets 11, 12 for the respective pairs of contacts 7, 8. The source 1 is installed between the sockets 11 and 12 so that the contacts 7, 8 are removably received in the respective sockets. The manner in which the inner end faces of the sockets 11, 12 are configurated to removably receive pairs of pin- or prong-shaped contacts is well known and forms no part of the present invention. The distance between the inner end faces of the sockets 11 and 12 equals or only slightly exceeds the combined length L of the body 2 and plugs 5, 6. A trough-shaped reflector 13 is installed in the housing 10 in such a way that it partially surrounds the body 2 and directs the radiation in a selected direction.

The housing 10 further contains a starter 14 and a timer 15, both in circuit with the contacts 7, 8 of a properly inserted source 1. The timer 15 is set to insure that, when the source 1 is caused to start with emission of radiation on actuation of the starter 14, the timer automatically interrupts the circuit after a preselected interval of time to thus insure that the user is not exposed to an excessive dosis of radiation such as could result in sunburn or other undesirable effects.

The housing 10 can be designed to comprise (and preferably comprises) two or more pairs of spaced-apart aligned sockets 11, 12 for an equal number of sources 1. The housing then further comprises a larger reflector 13 or several discrete reflectors, one for each source 1.

The exact design of the starter 14 and/or timer 15 forms no part of the invention.

An important advantage of the improved source 1 is that it comprises standard plugs and standard electric contacts or prongs. Therefore, such source can be installed in a sunlamp which comprises a pair of standard sockets for each source 1. Nevertheless, and since the length of the tubular body 2 plus the plugs 5, 6 deviates from the combined length of corresponding constituents of standard sources of fluorescent light, the source 1 can be installed in a specially designed sunlamp (such as the sunlamp 9 of FIG. 2) but is not insertable into a conventional light fixture. By the same token, the housing 10 of the sunlamp 9 cannot accept standard sources of light because the distance between the sockets 11 and 12 exceeds 437.4 mm.

Another important advantage of the improved source 1 and of the sunlamp which can accept one or more sources 1 is that the cost of the source need not exceed the cost of conventional sources of fluorescent light. Therefore, the improved source can be mass-produced at the cost of standard sources since it employs identical plugs and identical contacts. The fact that the length of its tubular body exceeds the standard length of 437.4 mm is of no consequence because the selection of a different length for the glass tubes (body 2) during manufacture does not increase the manufacturing cost. Moreover, the source 1 can be used in a sunlamp which is provided with standard auxiliary components, such as the starter 14 (e.g., a suitable transformer) and the timer 15. As mentioned above, the provision of a timer in circuit with the contacts of a properly inserted source 1 is desirable and advantageous because the person using the lamp is less likely to be accidentally exposed to an excessive dosage of ultraviolet radiation. Thus, even if the user fails to study the manual which, as a rule, must be furnished with the sunlamp, he or she cannot be exposed to excessive radiation in one sitting unless he or she selects to repeat the exposure after the timer 15 has opened the circuit.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the claims.

I claim:

1. A source of ultraviolet light, particularly in the UVA region, comprising a hollow elongated tubular body having first and second end portions and an outer diameter of approximately 25 mm; a plug at each of said end portions, the combined length of said tubular body and said plugs being between 440 and 450 mm; and electric contact means extending from each of said plugs.

2. The source of claim 1, wherein said length is approximately 445 mm.

3. The source of claim 1, wherein said length is between 444.5 and 445.5 mm.

4. A sunlamp, comprising a housing; spaced-apart aligned first and second sockets mounted in said housing; and a source of ultraviolet light, particularly in the UVA region, including a hollow elongated tubular body having first and second end portions and an outer diameter of approximately 25 mm, first and second plugs respectively provided at said first and second end portions, the combined length of said tubular body and said plugs being between 440 and 450 mm, and electric contact means extending from each of said plugs and removably received in the respective sockets.

5. The sunlamp of claim 4, wherein said housing comprises a reflector partially surrounding said source.

6. The sunlamp of claim 4, further comprising timer means installed in said housing in circuit with said contact means.

7. The sunlamp of claim 4, wherein each of said contact means comprises two contacts extending in substantial parallelism with the axis of said tubular body.

* * * * *